(12) United States Patent
Chien

(10) Patent No.: US 9,709,703 B2
(45) Date of Patent: Jul. 18, 2017

(54) OPHTHALMIC LENS MATERIAL, OPHTHALMIC LENS, AND METHOD FOR MAKING THE SAME

(71) Applicant: HON HAI PRECISION INDUSTRY CO., LTD., New Taipei (TW)

(72) Inventor: Hsiu-Wen Chien, New Taipei (TW)

(73) Assignee: HON HAI PRECISION INDUSTRY CO., LTD., New Taipei (TW)

( * ) Notice: Subject to any disclaimer, the term of this patent is extended or adjusted under 35 U.S.C. 154(b) by 0 days.

(21) Appl. No.: 14/941,083

(22) Filed: Nov. 13, 2015

(65) Prior Publication Data

US 2017/0123106 A1 May 4, 2017

(30) Foreign Application Priority Data

Nov. 3, 2015 (TW) .............................. 104136236 A

(51) Int. Cl.
| | |
|---|---|
| *C08F 2/46* | (2006.01) |
| *C08F 2/50* | (2006.01) |
| *C08G 61/04* | (2006.01) |
| *G02B 1/04* | (2006.01) |
| *C08F 220/28* | (2006.01) |
| *C08F 230/08* | (2006.01) |

(52) U.S. Cl.
CPC ............ *G02B 1/043* (2013.01); *C08F 220/28* (2013.01); *C08F 230/08* (2013.01); *C08F 2220/281* (2013.01)

(58) Field of Classification Search
CPC ...... G02B 1/043; C08F 220/28; C08F 230/08; C08F 2220/281
USPC ......................................... 522/172, 1; 520/1
See application file for complete search history.

(56) References Cited

U.S. PATENT DOCUMENTS

| | | | |
|---|---|---|---|
| 2010/0081772 A1* | 4/2010 | Zanini .............. | B29D 11/00134 525/450 |
| 2013/0168617 A1* | 7/2013 | Alli ....................... | C08G 77/442 252/589 |
| 2014/0377327 A1* | 12/2014 | Davis ..................... | A61K 45/06 424/429 |

OTHER PUBLICATIONS

Chung et al, Enhanced Adhesion of Dopamine Methacrylamide Elastomers via Viscoelasticity Tuning, Dec. 23, 2010, Biomacromolecules, 12, 342-347.*

* cited by examiner

*Primary Examiner* — Jessica E Whiteley
(74) *Attorney, Agent, or Firm* — Steven Reiss

(57) ABSTRACT

A method for making an ophthalmic lens includes following steps of mixing dopamine methacrylamide, a hydrophilic monomer, a cross-linking agent, and a photoinitiator to form a mixture; feeding the mixture into a mold and exposing the mixture to ultraviolet radiation, to cause the dopamine methacrylamide, the hydrophilic monomer, the photoinitiator, and the cross-linking agent to undergo a polymerization reaction. The disclosure also provides an ophthalmic lens made by above method, and an ophthalmic lens material making for the ophthalmic lens.

4 Claims, 1 Drawing Sheet

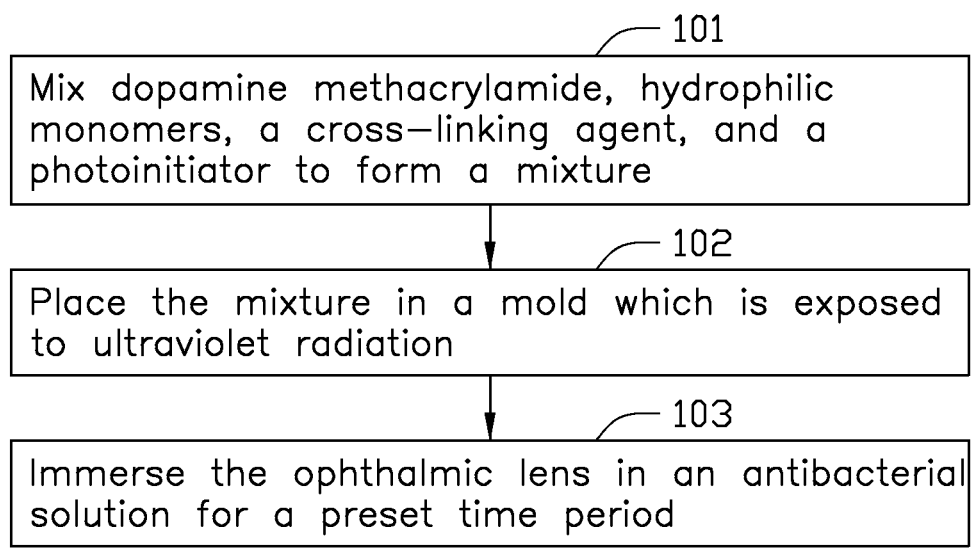

OPHTHALMIC LENS MATERIAL, OPHTHALMIC LENS, AND METHOD FOR MAKING THE SAME

FIELD

The subject matter herein generally relates to an ophthalmic lens, a method for making the ophthalmic lens, and an ophthalmic lens material for making the ophthalmic lens.

BACKGROUND

Contact lenses are commonly worn by users to correct vision, or for cosmetic or therapeutic reasons. Usually, antibacterial agents are disposed on the surface of a contact lens, to prevent a user from suffering from eye damage such as acute red eye or microbial keratitis.

BRIEF DESCRIPTION OF THE DRAWINGS

Implementations of the present technology will now be described, by way of example only, with reference to the attached FIGURES.

The FIGURE is a flowchart of an embodiment of a method for making an ophthalmic lens according to the present disclosure.

DETAILED DESCRIPTION

It will be appreciated that for simplicity and clarity of illustration, where appropriate, reference numerals have been repeated among the different FIGURES to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

The term "comprising," when utilized, means "including, but not necessarily limited to"; it specifically indicates open-ended inclusion or membership in the so-described combination, group, series and the like.

The FIGURE illustrates a flowchart of a method for making an ophthalmic lens in accordance with an exemplary embodiment. The exemplary method is provided by way of example, as there are a variety of ways to carry out the method. Each block shown in the FIGURE represents one or more processes, methods or subroutines, carried out in the exemplary method. Furthermore, the illustrated order of blocks is by example only and the order of the blocks can change. Additional blocks may be added or fewer blocks may be utilized, without departing from this disclosure. The exemplary method can begin at block 101.

At block 101, a mixture is formed by mixing dopamine methacrylamide, a hydrophilic monomer, a cross-linking agent, and a photoinitiator, wherein the dopamine methacrylamide has the chemical formula:

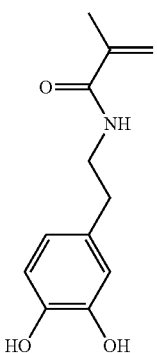 [SMILES: C=C(C)C(=O)NCCc1ccc(O)c(O)c1]

The dopamine methacrylamide has a mass percentage of about 0.5% to about 10% of a total mass of the mixture. The hydrophilic monomer has a mass percentage of about 88.95% to about 99.494% of a total mass of the mixture. The cross-linking agent has a mass percentage of about 0.001% to about 1% of a total mass of the mixture. The photoinitiator has a mass percentage of about 0.005% to about 0.05% of a total mass of the mixture.

The hydrophilic monomer may be selected from a group consisting of methylacrylic acid compounds and acrylic compounds, or any combination thereof, such as 2-hydroxyethyl methacrylate (HEMA), methyl methacrylate (MMA), poly(dimethylsiloxane), 3-methacryloxypropyltris(trimethylsiloxy)silane, N-vinyl pyrrolidone (NVP), glycidyl methacrylate, N,N-dimethylacrylamide, and methyl acrylate (MA), or any combination thereof.

The cross-linking agent may be selected from a group consisting of ethylene glycol dimethacrylate (EGDMA) and trimethylolpropane trimethacrylate (TMPTMA), or any combination thereof. The photoinitiator may be available commercially from Chemical Industries Basel (CIBA) Corporation as a clear liquid under the trade name "Irgacure-1173".

At block 102, the mixture is fed into a mold and is exposed to ultraviolet radiation, to cause the dopamine methacrylamide, the hydrophilic monomer, the photoinitiator, and the cross-linking agent in the mixture to undergo a polymerization reaction, thereby forming the ophthalmic lens. A time period for the ultraviolet irradiation is from about 10 min to about 30 min.

At block 103, the ophthalmic lens is immersed in an antibacterial solution containing an antibacterial agent for a preset period of time, allowing the antibacterial agent to be anchored to the catechol groups of the dopamine methacrylamide. As such, the antibacterial agent is not easily washed away by tears, thereby allowing the ophthalmic lens to maintain an antibacterial effect. When the antibacterial solution comprises metal ions (such as silver ions) functioning as the antibacterial agent, the catechol groups are able to reduce the metal ions to be nano metal particles which are anchored to the catechol groups. When the antibacterial agent comprises thiol groups or amine groups functioning as the antibacterial agent, the catechol groups react with the thiol groups or the amine groups to form covalent bonds, thereby anchoring the antibacterial agent to the dopamine methacrylamide. In other embodiments, the block 103 can be omitted from the method for making an ophthalmic lens, and such a step can be performed before wearing the ophthalmic lens.

Example 1

A mixture is formed by mixing dopamine methacrylamide, 2-hydroxyethyl methacrylate, poly(dimethylsiloxane), ethylene glycol dimethacrylate, and Irgacure-1173. The dopamine methacrylamide has a mass percentage of 1% of a total mass of the mixture. The 2-hydroxyethyl methacrylate has a mass percentage of 60% of a total mass of the mixture. The poly(dimethylsiloxane) has a mass percentage of 38.94% of a total mass of the mixture. The ethylene glycol dimethacrylate has a mass percentage of 0.05% of a total mass of the mixture. Irgacure-1173 has a mass percentage of 0.01% of a total mass of the mixture. The mixture is fed into a mold and is exposed to ultraviolet radiation for 25 min, thereby forming an ophthalmic lens.

Example 2

A mixture is formed by mixing dopamine methacrylamide, 2-hydroxyethyl methacrylate, 3-methacryloxypropyletris (trimethylsiloxy) silane, ethylene glycol dimethacrylate, and Irgacure-1173. The dopamine methacrylamide has a mass percentage of 10% of a total mass of the mixture. The 2-hydroxyethyl methacrylate has a mass percentage of 45% of a total mass of the mixture. The 3-methacryloxypropyletris (trimethylsiloxy) silane has a mass percentage of 43.98% of a total mass of the mixture. The ethylene glycol dimethacrylate has a mass percentage of 1% of a total mass of the mixture. Irgacure-1173 has a mass percentage of 0.02% of a total mass of the mixture. The mixture is fed into a mold and is exposed to ultraviolet radiation for 30 min, thereby forming an ophthalmic lens.

Example 3

A mixture was formed by mixing dopamine methacrylamide, methyl methacrylate, 3-methacryloxypropyletris (trimethylsiloxy) silane, ethylene glycol dimethacrylate, and Irgacure-1173. The dopamine methacrylamide has a mass percentage of 5% of a total mass of the mixture. The methyl methacrylate has a mass percentage of 30% of a total mass of the mixture. The 3-methacryloxypropyletris (trimethylsiloxy) silane has a mass percentage of 64.94% of a total mass of the mixture. The ethylene glycol dimethacrylate has a mass percentage of 0.05% of a total mass of the mixture. Irgacure-1173 has a mass percentage of 0.01% of a total mass of the mixture. The mixture was fed into a mold and was exposed to ultraviolet radiation for 28 min, thereby forming an ophthalmic lens.

Example 4

The ophthalmic lens obtained from the example 1 was immersed in a silver nitrate solution having a concentration of 1 mmol/L for 12 hours, thereby causing silver nano particles to be anchored to the catechol groups of the dopamine methacrylamide comprised in the ophthalmic lens.

Example 5

The ophthalmic lens obtained from the example 2 was immersed in a silver nitrate solution having a concentration of 15 mmol/L for 16 hours, thereby causing silver nano particles to be anchored to the catechol groups of the dopamine methacrylamide comprised in the ophthalmic lens.

Example 6

The ophthalmic lens obtained from the example 3 was immersed in a antibacterial peptide solution for 20 hours, thereby causing antibacterial peptides comprised in the antibacterial peptide solution to be anchored to the catechol groups of the dopamine methacrylamide comprised in the ophthalmic lens.

An ophthalmic lens material used in the method to make the ophthalmic lens is provided according the present disclosure. The ophthalmic lens material comprises dopamine methacrylamide, a hydrophilic monomer, a cross-linking agent, and a photoinitiator. The dopamine methacrylamide has a mass percentage of about 0.5% to about 10% of a total mass of the ophthalmic lens material. The hydrophilic monomer has a mass percentage of about 88.95% to about 99.494% of a total mass of the ophthalmic lens material. The cross-linking agent has a mass percentage of about 0.001% to about 1% of a total mass of the ophthalmic lens material. The photoinitiator has a mass percentage of about 0.005% to about 0.05% of a total mass of the ophthalmic lens material. When the ophthalmic lens material is exposed to ultraviolet radiation, the dopamine methacrylamide, the hydrophilic monomer, the photoinitiator, and the cross-linking agent undergo a polymerization reaction, thereby forming an ophthalmic lens.

An ophthalmic lens made by the method is provided according the present disclosure. The ophthalmic lens is formed by exposing a mixture of the dopamine methacrylamide, the hydrophilic monomer, the photoinitiator, and the cross-linking agent to ultraviolet radiation to cause the mixture to undergo a polymerization reaction. The ophthalmic lens can be a contact lens or an intraocular lens. The dopamine methacrylamide has a mass percentage of about 0.5% to about 10% of a total mass of the dopamine methacrylamide, the hydrophilic monomer, the cross-linking agent, and the photoinitiator. The hydrophilic monomer has a mass percentage of about 88.95% to about 99.494% of a total mass of the dopamine methacrylamide, the hydrophilic monomer, the cross-linking agent, and the photoinitiator. The cross-linking agent has a mass percentage of about 0.001% to about 1% of a total mass of the dopamine methacrylamide, the hydrophilic monomer, the cross-linking agent, and the photoinitiator. The photoinitiator has a mass percentage of about 0.005% to about 0.05% of a total mass of the dopamine methacrylamide, the hydrophilic monomer, the cross-linking agent, and the photoinitiator.

It is to be understood, even though information and advantages of the present embodiments have been set forth in the foregoing description, together with details of the structures and functions of the present embodiments, the disclosure is illustrative only; changes may be made in detail, especially in matters of shape, size, and arrangement of parts within the principles of the present embodiments to the full extent indicated by the plain meaning of the terms in which the appended claims are expressed.

What is claimed is:

1. A method for making an ophthalmic lens comprising:
   mixing dopamine methacrylamide, a hydrophilic monomer, a cross-linking agent, and a photoinitiator to form a mixture; and
   feeding the mixture into a mold and exposing the mixture to ultraviolet radiation, thereby causing the dopamine methacrylamide, the hydrophilic monomer, the photoinitiator, and the cross-linking agent to undergo a polymerization reaction;
   wherein the dopamine methacrylamide has a mass percentage of 0.5% to 10% of a total mass of the mixture; the hydrophilic monomer has a mass percentage of 88.95% to 99.494% of the total mass of the mixture; the cross-linking agent has a mass percentage of 0.001% to 1% of the total mass of the mixture; the photoinitiator has a mass percentage of 0.005% to 0.05% of the total mass of the mixture.

2. The method of claim 1, wherein the hydrophilic monomer is selected from a group consisting of methylacrylic acid compounds and acrylic compounds, and any combination thereof.

3. The method of claim 1, wherein the hydrophilic monomer is selected from a group consisting of 2-hydroxyethyl methacrylate, methyl methacrylate, poly(dimethylsiloxane), 3-methacryloxypropyletris(trimethylsiloxy)silane, N-vinyl pyrrolidone, glycidyl methacrylate, N,N-dimethylacrylamide, and methyl acrylate, and any combination thereof.

4. The method of claim 1, further comprising:
   immersing the ophthalmic lens in an antibacterial solution containing an antibacterial agent for a preset period of time, to cause the antibacterial agent to be anchored to catechol groups of the dopamine methacrylamide.

* * * * *